United States Patent
Fernfors et al.

(10) Patent No.: US 8,188,332 B2
(45) Date of Patent: May 29, 2012

(54) DISPOSABLE COVER FOR USE IN AN INCUBATOR FOR PREMATURE INFANTS

(75) Inventors: Ingemar Fernfors, Mölndal (SE); Anna-Gerd Doverbo, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 477 days.

(21) Appl. No.: 12/447,735

(22) PCT Filed: Dec. 22, 2006

(86) PCT No.: PCT/SE2006/001500
§ 371 (c)(1),
(2), (4) Date: Apr. 29, 2009

(87) PCT Pub. No.: WO2008/079060
PCT Pub. Date: Jul. 3, 2008

(65) Prior Publication Data
US 2011/0152641 A1    Jun. 23, 2011

(51) Int. Cl.
*A61F 13/15* (2006.01)
*A61B 5/22* (2006.01)
*B65B 61/26* (2006.01)

(52) U.S. Cl. .................. 604/358; 53/131.2; 600/362

(58) Field of Classification Search ............. 604/356, 604/358, 361; 53/131.2; 600/309, 362
See application file for complete search history.

(56) References Cited

U.S. PATENT DOCUMENTS

| | | | | | |
|---|---|---|---|---|---|
| 1,577,012 | A | * | 3/1926 | Crane | 177/8 |
| 2,598,532 | A | * | 5/1952 | Gibbon | 600/22 |
| 3,072,969 | A | * | 1/1963 | Du Bois | 264/509 |
| 3,194,857 | A | * | 7/1965 | White | 425/105 |
| 3,407,414 | A | * | 10/1968 | Burns et al. | 5/487 |
| 3,521,624 | A | * | 7/1970 | Rovee et al. | 128/849 |
| 3,576,039 | A | * | 4/1971 | Roberts | 5/484 |
| 3,670,345 | A | * | 6/1972 | Doll et al. | 5/484 |
| 3,759,417 | A | * | 9/1973 | Armstrong et al. | 221/85 |
| 3,994,217 | A | * | 11/1976 | Archila | 101/35 |
| 4,038,973 | A | * | 8/1977 | Moore | 600/22 |
| 4,101,366 | A | * | 7/1978 | Teraoka et al. | 156/378 |
| 4,128,686 | A | * | 12/1978 | Kyle et al. | 428/219 |
| 4,342,038 | A | * | 7/1982 | Lemelson | 346/9 |

(Continued)

FOREIGN PATENT DOCUMENTS

EP    1180370 A1    2/2002

(Continued)

OTHER PUBLICATIONS

Oddie, S., et al., Measurement of urine output by weighing nappies, Arch Dis Child Fetal Neonatal Ed. 2004; 89:F180-F181.*

(Continued)

*Primary Examiner* — Melanie Hand
*Assistant Examiner* — Paula Craig
(74) *Attorney, Agent, or Firm* — Buchanan Ingersoll & Rooney PC

(57) ABSTRACT

The invention refers to a disposable cover for use in an incubator for premature infants comprising a moisture-pervious surface layer and a preferably moisture-impervious back sheet, wherein the total weight of the cover before use is communicated to the caregiver by indication on said cover, a label accompanying said cover or on the package for said cover. The cover may further be provided with a wetness indicator.

20 Claims, 1 Drawing Sheet

U.S. PATENT DOCUMENTS

| | | | | |
|---|---|---|---|---|
| 4,543,766 A * | 10/1985 | Boshinski | | 53/64 |
| 4,662,528 A * | 5/1987 | Slat | | 215/12.2 |
| 4,681,576 A * | 7/1987 | Colon et al. | | 604/361 |
| 4,695,496 A * | 9/1987 | Lee | | 428/95 |
| 4,793,428 A * | 12/1988 | Swersey | | 177/144 |
| 4,846,182 A * | 7/1989 | Fogt et al. | | 600/362 |
| 5,031,642 A * | 7/1991 | Nosek | | 600/584 |
| 5,252,374 A * | 10/1993 | Larsonneur | | 428/77 |
| 5,372,258 A * | 12/1994 | Daneshvar | | 206/534 |
| 5,376,761 A * | 12/1994 | Koch et al. | | 177/145 |
| 5,884,238 A * | 3/1999 | Noll et al. | | 702/150 |
| 6,210,329 B1 * | 4/2001 | Christmas et al. | | 600/437 |
| 6,231,556 B1 * | 5/2001 | Osborn, III | | 604/385.08 |
| 6,272,780 B1 * | 8/2001 | Satamian | | 40/638 |
| 6,399,853 B1 * | 6/2002 | Roe et al. | | 604/362 |
| 6,592,043 B1 * | 7/2003 | Britton | | 235/492 |
| 6,603,400 B1 * | 8/2003 | Shoobridge | | 340/572.1 |
| 6,956,175 B1 * | 10/2005 | Daly et al. | | 177/1 |
| 7,158,916 B1 * | 1/2007 | Yarian | | 702/173 |
| 2002/0163178 A1 * | 11/2002 | Williams | | 283/62 |
| 2004/0090642 A1 * | 5/2004 | Hikita | | 358/1.11 |
| 2004/0243080 A1 * | 12/2004 | Baer | | 604/378 |
| 2005/0055768 A1 * | 3/2005 | Assink | | 5/81.1 R |
| 2005/0155875 A1 * | 7/2005 | Snell | | 206/223 |
| 2005/0195085 A1 | 9/2005 | Cretu-Petra | | |
| 2005/0234414 A1 | 10/2005 | Liu | | |
| 2006/0069362 A1 | 3/2006 | Odorzynski et al. | | |
| 2006/0075329 A1 * | 4/2006 | Sullivan et al. | | 715/507 |
| 2006/0100599 A1 * | 5/2006 | Engel et al. | | 604/385.06 |
| 2006/0206078 A1 * | 9/2006 | Corlett | | 604/385.02 |
| 2006/0276921 A1 * | 12/2006 | Verstraeten | | 700/95 |
| 2007/0057050 A1 * | 3/2007 | Kuhno et al. | | 235/383 |
| 2007/0204691 A1 * | 9/2007 | Bogner et al. | | 73/432.1 |
| 2007/0215709 A1 * | 9/2007 | Baude et al. | | 235/492 |
| 2008/0074271 A1 * | 3/2008 | Hodges | | 340/572.7 |
| 2008/0103414 A1 * | 5/2008 | Song | | 600/573 |

FOREIGN PATENT DOCUMENTS

| | | |
|---|---|---|
| EP | 1035818 B1 | 4/2002 |
| EP | 1210277 B1 | 10/2003 |
| JP | 2002-224093 A | 8/2002 |
| RU | 2 184 517 | 7/2002 |
| WO | WO 2004/021944 A1 | 3/2004 |

OTHER PUBLICATIONS

Bronislava Banar, Height of a Newborn Baby from The Physics Factbook TM, hypertextbook.com, 2003.*

An English Translation of the Office Action dated Jun. 2, 2010 issued in the corresponding Russian Application No. 2009128217.

International Search Report (PCT/ISA/210) for PCT/SE2006/001500, completed Jun. 18, 2007.

Written Opinion (PCT/ISA/237) for PCT/SE2006/001500, completed Jun. 18, 2007.

* cited by examiner

DISPOSABLE COVER FOR USE IN AN INCUBATOR FOR PREMATURE INFANTS

This application is a national phase of PCT/SE2006/001500 filed Dec. 22, 2006.

TECHNICAL AREA

The present invention relates to a disposable cover for use in an incubator for premature infants. The cover comprises a moisture-pervious sheet intended to face the premature infant during use and a back sheet, preferably substantially moisture-impervious.

BACKGROUND

Premature infants come into the world earlier than full-term infants. Prematurity occurs when a pregnancy lasts fewer than 37 weeks; full-term infants are born 38 to 42 weeks after the mother's last menstrual period. Premature infants borne as early as after 22 to 23 weeks may survive, this is however rare. After 25 to 26 week the infants have quite high chance of surviving, about 44% of the infants born between 25 and 26 week survive.

Full-term infants normally weigh around 2.5-5 kg at the time of birth. Due to many recent advances, more than 90% of premature babies who weigh 800 grams or more survive. Those who weigh more than 500 grams have a 40% to 50% chance of survival, although the risk for complications is greater.

Premature infants have many special needs that make their care different from that of full-term infants, which is why they often begin their lives after delivery in a neonatal intensive care unit. The neonatal intensive care unit is designed to provide an atmosphere that limits stress to the infant and meets basic needs of warmth, nutrition, and protection to assure proper growth and development.

In most neonatal intensive care unit the nurses try to concentrate their care into discrete sessions and otherwise allow the infants to sleep undisturbed. Some of the tasks which are done regularly are; measuring the infant's temperature, mouth care, bathing and changing of diapers or covers. In order not to have something chafing against the sensitive premature infant's skin an absorbent cover may be placed in the incubator instead of a diaper being put on the infant. In order to fit into the incubator the large cover intended for adult care is cut into a suitable size. At regular intervals these small covers are changed, up to one time per hour in order to control if the baby has urinated. Before and after use the nurses weigh the diapers and/or covers in order to keep track of the infants discharge of urine and faeces. This is important information in order to assess if the basal functions are functioning correctly, such as for example the kidney and the urinary tracts, and as a further step, in order for the caregivers to compare the input of nutrition and the discharge of urine and faeces for an evaluation of the nutrition uptake of the infant. Since it may be difficult to detect if the baby has urinated just by looking into the incubator when the baby is lying on top of the cover, the covers are often changed more frequently than necessary. This results in more handling of the small premature infants than necessary, which are known to feel best with as few factors of disturbance as possible. For the personnel working at these departments the cutting of the covers and the weighing of said covers before and after use are extra working moments. Cutting the large cover into smaller pieces further leads to open side edges of the covers often containing cellulose fibers, which may cause the small cellulose fibers to spread and dust in the incubator.

EP1180370 describes a covering sheet for bedding articles, such as mattress and pillow covering sheet, having a surface area from 15 m$^2$ to 0.3 m$^2$. However this is a very broad range with no indications on how to adjust the covering sheet in width and length in order to be of a size that may fit into an incubator.

JP2002224093 discloses an electronic excretion sensor for diaper or urine absorption pad that calculates the amount of excretion absorbed by diaper by sensor output.

WO2004021944 discloses a sensing device in the form of a magnetoelastic film for detecting wetness in absorbent articles such as bed protector. US20050234414 and US20060069362 disclose diapers with wetness indication by visible colour change. US 20050195085 describes an electronic wetness sensors for diapers.

In view of the above stated problems in the field of care of premature infants and in view of the prior art there is still a need for a cover specially adapted for use in an incubator, which cover is easy to use and further reduces the working moments of the caregivers and prevent unnecessary handling of the sensitive premature infants.

SUMMARY

In view of this prior art it is an object of the present invention to provide a disposable cover specially adapted for an incubator for premature infants which disposable cover further reduces the working moments of the caregivers and is easy to use.

The above defined problems are solved by the present invention by a disposable cover for use in an incubator for premature infants, said cover having a defined total weight before use which weight is communicated to the caregiver by indication on said cover, a label accompanying said cover or on the package for said cover.

In one aspect said disposable cover has a defined weight within a tolerance of ±1 g, preferably ±0.5 g.

In one embodiment the total weight of said cover is printed onto said cover. In another embodiment the total weight of said cover is embossed onto said cover. In a further embodiment the total weight is provided as a note in connection with said cover. In still a further embodiment the total weight of said cover is printed or marked onto the package of said cover.

In a further embodiment said disposable cover comprises a wetness indicator.

In still a further embodiment said disposable cover comprises a sensor indicating the presence of proteins (albumin), blood and/or unwanted bacteria in the urine.

In one aspect the cover is a laminate comprising a surface layer consisting of an apertured plastic film or a nonwoven material and a preferably moisture-impervious backsheet.

In a further aspect the cover is a laminate comprising a surface layer consisting of synthetic fibers or an apertured plastic film and a preferably moisture-impervious backsheet.

In a still further aspect the cover is a laminate consisting of a surface layer being an apertured plastic film or a nonwoven material and a preferably moisture-impervious backsheet. This however does not exclude that other components not forming part of the laminate structure, such as a wetness indicator or other sensor, are included.

BRIEF DESCRIPTION OF THE DRAWINGS

Aspects of the present disclosure will now be described in more detail, with reference to the appended drawings showing example embodiments of the disclosure, wherein.

DETAILED DESCRIPTION

Figure 1:
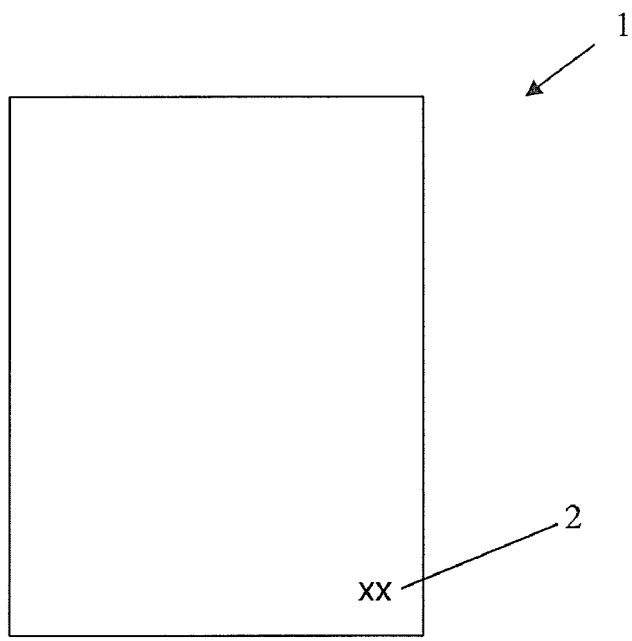
FIG. 1 is a schematic perspective view of a disposable according to various embodiments of the present invention.
Figure 2:
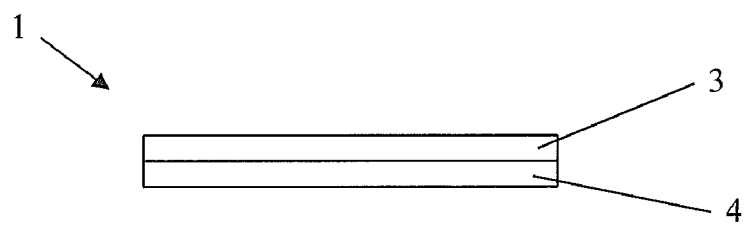
FIG. 2 is a cross-section view of a disposable according to various embodiments of the present invention.

According to the present invention, an exemplary embodiment of which is shown in FIGS. 1 and 2, a disposable cover 1 intended for use in an incubator for premature infants is provided, comprising a moisture-pervious sheet 3 intended to face the premature infant during use and a preferably moisture-impervious backsheet 4. In order to reduce the working moment of weighing the disposable cover before use, the specified total weight before use of said cover may be communicated to the caregiver by indication 2 on said cover, a label accompanying said cover or on the package for said cover.

In one aspect of the invention the disposable covers are each weighed, in the production line or after production, and the specific weight of the cover subsequently printed or in any way marked onto said cover or onto a label accompanying said cover. In another aspect each cover is produced with such a high accuracy in terms of weight that it is possible to indicate the total weight of one disposable cover on the package, this meaning that all the disposable covers comprised in the package substantially have the same weight. It would of course also in this later case be possible to indicate the weight onto the cover or on an accompanying label.

The discharge of urine from a premature infant may be in the range from about 2 ml (about 2 g) to about 0.5 dl (about 50 g), so in order for the caregiver to perform a proper assessment of the discharge of urine and faeces and thus an analysis of the infants health status, the tolerance for the weight indication preferably is ±1.0 g, more preferably ±0.5 g.

This accuracy may be achieved by using as surface layer a prefabricated material, preferably synthetic fibres, since these materials often have an constant density and a plastic film, for example a polypropylene film, as backsheet material. Alternatively, a prefabricated laminate, comprising the same materials as above, will also have a constant density.

In order to keep the weight of the cover as constant as possible after the weight is determined, the cover may be packed separately in a moisture-impervious package. An example of such a moisture-impervious package is disclosed in EP 1210277.

In a preferred embodiment, in order to fit into the incubator said disposable cover has a length of 10-60 cm and a width of 5-40 cm, preferably a length of 12-50 cm and a width of 6-30 cm, more preferably a length of 15-45 cm and a width of 7-25 cm.

Since the premature infants are small in comparison with the incubator, it is not of great importance that said cover extends throughout the entire incubator, the essential thing is that it covers the area which may be wetted during the discharge of urine and/or faeces. Sometimes it may even be advantageous not to cover the entire bottom of the incubator since a smaller cover will be easier to change and also to handle, for example during weighing of said cover.

The cover of the present invention is a laminate made up of different layers comprising at least a moisture-pervious sheet and a second, preferably moisture-impervious backsheet.

The moisture-pervious surface layer may be of any conventional type such as a nonwoven material, e g spunbonded, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and manmade fibres. The surface layer material may further be composed of tow fibres, which may be bonded to each other in a bonding pattern, as e.g. disclosed in EP-A-1 035 818. Further examples of surface layer materials are porous foams, apertured plastic films etc. The materials suited as surface layer materials should be soft and non-irritating to the skin and be readily penetrated by body fluid. The surface layer may also comprise absorptive means i.e. comprising for example absorbent fibers.

The backsheet may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. Further the backsheet material may optionally be breathable.

The disposable cover may further comprise an absorbent layer, dispersed between the surface layer and the backsheet.

Since the cover may be used mainly in order to collect and consequently weigh the discharge of urine and faeces, the cover of the present invention may in one preferred embodiment be a laminate comprising a surface layer consisting of an apertured plastic film or a nonwoven material and a preferably moisture-impervious backsheet. This means that said cover will not comprise an absorbent layer.

In a further preferred embodiment the cover of the present invention is a laminate comprising a surface layer consisting of synthetic fibers or an apertured plastic film and a preferably moisture-impervious backsheet. The advantage of such a laminate is that it absorbs essentially no moisture from the surroundings which could have an impact on the weight of said cover.

In a further embodiment, in order to reduce unnecessary handling of the premature infants, the disposable cover may further comprise a wetness indicator, indicating when the infant has urinated, which may otherwise be difficult to detect, especially if the urine has very little colour. For example, a disposable cover including a wetness indicator is weighed after the wetness indicator indicates that the disposable cover has become wet. The wetness indicator may be located on any side of the surface layer, provided that the wetness indicator remains visible from the body contacting side of the disposable cover. The wetness indicator may comprise a visible change that is selected from the group consisting of a colour change, a graphic change or a combination there of.

In one embodiment the wetness indicator is a chemical compound being colourless in its dry state and changes colour to a humanly visible colour such as, but not limited to, green, blue, red, pink or another colour when exposed to moisture and especially urine. In another embodiment the chemical compound instead comprises one or more colours in its dry state and turns colourless or changes colour upon wetting. The wetness indicator or substance may further be a chemical compound which dyes with pH transition, preferably at about pH8-9, i.e. a pH-indicator, such as litmus that is absorbed onto a filter paper i.e. a litmus paper. In another embodiment the indicator consists of a coloured graphic, which may either turn colourless or change graphic or colour of the graphic upon wetting.

In still another embodiment the wetness indicator is an electronic humidity or wetness sensor.

The disposable cover may also comprise sensors indicating presence of proteins (albumin), blood or unwanted bacteria in the urine, preferably by a readily visible colour indication.

Such wetness indicators or other sensors that may be incorporated are well known in the art and will not be further described herein.

In order to prevent contact of the chemical compound with the baby, the indicator may be covered with a material layer, the indicator may for example be dispersed in a highly absorbent tissue layer placed between the backsheet and the surface layer in order for the urine to spread well on the layer comprising the indicator and the indicating colour to be readily visible. In order to increase the visibility of such a colour change the wetness indicator the layer comprising the wetness indicator may be arranged in such a way that a tab of said layer is protruding horizontally from said cover.

The invention claimed is:

1. A packaged disposable cover for an incubator for premature infants, the packaged disposable cover comprising a package and at least one disposable cover, the package enclosing the disposable cover prior to use, the disposable cover being dimensioned and configured for use in an incubator for premature infants, the disposable cover comprising a moisture-pervious surface layer intended to face the premature infant during use and a back sheet, wherein the total weight of said disposable cover before use is communicated to a caregiver by indication on said cover, wherein said disposable cover has a width of 5-40 cm and a length of 10-60 cm;
   said disposable cover has a defined weight within a tolerance of ±1 g;
   the total weight of said disposable cover is printed, marked, or embossed onto said cover; and
   the total weight is the actual weight of the individual disposable cover.

2. The disposable cover according to claim 1, wherein the total weight of said disposable cover before use is printed onto said cover.

3. The disposable cover according to claim 1, wherein the total weight of said disposable cover before use is embossed onto said cover.

4. The disposable cover according to claim 1, wherein the disposable cover comprises a wetness indicator.

5. The disposable cover according to claim 4, wherein said wetness indicator comprises a colorant changing colour upon wetting.

6. The disposable cover according to claim 5, wherein said colorant is a pH-indicator.

7. The disposable cover according to claim 1, wherein the disposable cover comprises a sensor indicating the presence of proteins in the urine, blood in the urine or unwanted bacteria in the urine.

8. The disposable cover according to claim 1, wherein said cover is a laminate of the moisture pervious surface layer and the back sheet, wherein the moisture-pervious surface layer is an apertured plastic film or a nonwoven material and the back sheet is moisture-impervious.

9. The disposable cover according to claim 1, wherein said cover is a laminate comprising the moisture pervious surface layer and the back sheet, wherein the moisture-pervious surface layer is of synthetic fibers or an apertured plastic film and the back sheet is moisture-impervious.

10. The disposable cover according to claim 1, wherein said disposable cover has a defined weight within a tolerance of ±0.5 g.

11. The disposable cover according to claim 1, wherein said disposable cover has a length of 12-50 cm and a width of 6-30 cm.

12. The disposable cover according to claim 1, wherein said disposable cover has a length of 15-45 cm and a width of 7-25 cm.

13. The disposable cover according to claim 1, wherein the disposable cover comprises a sensor indicating the presence of albumin, in the urine.

14. The disposable cover according to claim 1, wherein the disposable cover comprises a sensor indicating the presence of blood in the urine.

15. A method of monitoring basal functions of a premature infant, comprising:
   individually weighing a disposable cover before use for an incubator, the disposable cover comprising a moisture-pervious surface layer intended to face the premature infant during use and a back sheet;
   indicating the individual before use weight of each said disposable cover on said cover, a label accompanying said cover or on a package for said cover;
   placing the disposable cover in the incubator with the premature infant; and
   weighing the disposable cover after use.

16. The method of claim 15, wherein the disposable cover includes a wetness indicator and the disposable cover is weighed after the wetness indicator indicates that the disposable cover has become wet.

17. The method of claim 15, wherein the disposable cover is individually weighed by a manufacturer and wrapped in a moisture impervious package prior to use.

18. A method of monitoring basal functions of a premature infant, comprising:
   determining the weight of a disposable cover before use for an incubator, the disposable cover comprising a moisture-pervious surface layer intended to face the premature infant during use and a back sheet;
   indicating the individual before use weight of each said disposable cover on said cover, a label accompanying said cover or on a package for said cover;
   placing the disposable cover in the incubator with the premature infant; and
   weighing the disposable cover after use.

19. The method of claim 18, wherein the disposable cover includes a wetness indicator and the disposable cover is weighed after the wetness indicator indicates that the disposable cover has become wet.

20. The disposable cover according to claim 18, wherein the determined weight is the actual weight of the disposable cover.

* * * * *